US008309356B2

(12) United States Patent
Glazer

(10) Patent No.: US 8,309,356 B2
(45) Date of Patent: Nov. 13, 2012

(54) PSEUDOCOMPLEMENTARY OLIGONUCLEOTIDES FOR TARGETED GENE THERAPY

(75) Inventor: Peter M. Glazer, Gulford, CT (US)

(73) Assignee: Yale University, New Haven, CT (US)

( * ) Notice: Subject to any disclaimer, the term of this patent is extended or adjusted under 35 U.S.C. 154(b) by 167 days.

(21) Appl. No.: 12/753,016

(22) Filed: Apr. 1, 2010

(65) Prior Publication Data

US 2011/0086905 A1     Apr. 14, 2011

Related U.S. Application Data

(60) Provisional application No. 61/165,715, filed on Apr. 1, 2009.

(51) Int. Cl.
*C12N 15/87* (2006.01)
*A61K 31/70* (2006.01)
*C07H 21/04* (2006.01)
(52) U.S. Cl. ......... 435/463; 514/44; 536/23.1; 536/24.5
(58) Field of Classification Search ........................ None
See application file for complete search history.

(56) References Cited

U.S. PATENT DOCUMENTS

| | | |
|---|---|---|
| 3,832,253 A | 8/1974 | Palma |
| 3,854,480 A | 12/1974 | Zaffaroni |
| 4,452,775 A | 6/1984 | Kent |
| 4,667,013 A | 5/1987 | Reichle |
| 4,675,189 A | 6/1987 | Kent |
| 4,748,034 A | 5/1988 | Rham |
| 5,034,506 A | 7/1991 | Summerton |
| 5,075,109 A | 12/1991 | Tice |
| 5,133,974 A | 7/1992 | Paradissis |
| 5,239,660 A | 8/1993 | Ooi |
| 5,407,686 A | 4/1995 | Patel |
| 5,527,675 A | 6/1996 | Coull |
| 5,539,082 A | 7/1996 | Nielsen |
| 5,623,049 A | 4/1997 | Lobberding |
| 5,714,331 A | 2/1998 | Buchardt |
| 5,736,152 A | 4/1998 | Dunn |
| 5,736,336 A | 4/1998 | Buchardt |
| 5,773,571 A | 6/1998 | Nielsen |
| 5,786,571 A | 7/1998 | Bethel |
| 6,010,908 A * | 1/2000 | Gruenert et al. .............. 435/463 |
| 6,919,208 B2 | 7/2005 | Levy |

OTHER PUBLICATIONS

Abes, et al., "Endosome trapping limits the efficiency of splicing correction by PNA-oligolysine conjugates", J. Controll. Rel., 110:595-604 (2006).Braasch, et al., Chem. Biol., 8(1):1-7 (2001).
Braasch, et al., "Locked nucleic acid (LNA): fine-tuning the recognition of DNA and RNA", Chem. Biol., 8(1):1-7 (2001).
Chan, et al., "Targeted correction of an episomal gene in mammalian cells by a short DNA fragment tethered to a triplex-forming oligonucleotide", J. Biol. Chem., 274(17):11541-11548 (1999).
Datta, et al., "Triplex-induced Recombination in Human Cell-free Extracts," J. Biol. Chem., 276:18018-18023 (2001).
Horne, et al., "Recognition of Mixed-Sequence Duplex DNA by Alternate-Strand Triple-Helix Formation", J. Am. Chem. Soc., 112:2435-2437 (1990).
Hu, et al., "Reaction parameters of targeted gene repair in mammalian cells", Mol. Biotech., 29:197-210 (2005).
Huang, et al., "Functional silencing of hepatic microsomal glucose-6-phosphatase gene expression in vivo by adenovirus-mediated delivery of short hairpin RNA", FEBS Lett., 558(1-3):69-73 (2004).
Igoucheva, et al., "Transcription affects formation and processing of intermediates in oligonucleotide-mediated gene alteration", Nucleic Acids Res., 31:2659-2670 (2003).
Izvolsky, et al., "Sequence-specific protection of duplex DNA against restriction and methylation enzymes by pseudocomplementary PNAs", Biochemistry, 10908-10913 (2000).
Jasin, "Genetic manipulation of genomes with rare-cutting endonucleases", Trends Genet., 12:224-228 (1996).
Kim, et al., "Efficient sequence-directed psoralen targeting using pseudocomplementary Peptide nucleic acids", Bioconjug. Chem., 18:567-572 (2007).
Kim, et al., "Site-directed gene mutation at mixed sequence targets by psoralen-conjugated pseudo-complementary peptide nucleic acids", Nucleic Acids, 35:7604-7613 (2007).
Knauert, et al., "Triplex-stimulated intermolecular recombination at a single-copy genomic target", Mol. Therapy, 14:392-400 (2006).
Lahoud, et al., "Properties of pseudo-complementary DNA substituted with weakly pairing analogs of guanine or cytosine", Nucleic Acids Research, 36(22):6999-7008 (2008).
Lohse, et al., "Double duplex invasion by peptide nucleic acid: a general principle for sequence-specific targeting of double-stranded DNA", Proc. Natl. Acad. Sci. USA, 96:11804-11808 (1999).
Lorenz, et al., "Steroid and lipid conjugates of siRNAs to enhance cellular uptake and gene silencing in liver cells", Bioorg. Med. Chem. Lett., 14(19):4975-4977 (2004).
Ma, et al., "Nuclease-resistant external guide sequence-induced cleavage of target RNA by human ribonuclease P", Antisense Nucleic Acid Drug Dev., 8(5):415-26 (1998).
Majumdar, et al., "Cell cycle modulation of gene targeting by a triple helix-forming oligonucleotide", J. Biol. Chem., 278(13):11072-7 (2003).
Nyce and Metzger, "DNA antisense therapy for asthma in an animal model", Nature, 385(6618):721-5 (1997).
Olsen, et al., "Genomic sequence correction by single-stranded DNA oligonucleotides: role of DNA synthesis and chemical modifications of the oligonucleotide ends", J. Gene Med., 7:1534-1544 (2005).

(Continued)

*Primary Examiner* — Tracy Vivlemore
(74) *Attorney, Agent, or Firm* — Pabst Patent Group LLP

(57) ABSTRACT

Compositions and methods for targeted gene therapy are disclosed. Compositions containing double duplex-forming pseudocomplementary oligonucleotides are administered in combination with a donor oligonucleotide that is homologous to a target sequence on a double-stranded DNA molecule in need of repair or replacement. By activating cellular mechanisms involved in DNA synthesis, repair and recombination, the double duplex-forming pseudocomplementary oligonucleotides can introduce one or more mutations at a site of interest by increasing the efficiency of targeted recombination of the donor oligonucleotide. The pseudocomplementary oligonucleotides/donor oligonucleotide compositions may be administered in combination with a second therapeutic agent that enhances access of the pseudocomplementary oligonucleotides and/or the donor oligonucleotide to the target site, an agent that enhances or increases DNA repair or recombination, or an agent that enhances uptake or delivery of the oligonucleotides.

21 Claims, 4 Drawing Sheets

OTHER PUBLICATIONS

Rogers, et al., "Site-directed recombination via bifunctional PNA-DNA conjugates", Proc. Natl. Acad. Sci U.S.A., 99(26):16695-16700 (2002).

Rump, et al., "Modification of the plasma clearance and liver uptake of steroid ester-conjugated oligodeoxynucleotides by association with (lactosylated) low-density lipoprotein", Biochem. Pharmacol. 59(11):1407-1416 (2000).

Soutschek, et al., "Therapeutic silencing of an endogenous gene by systemic administration of modified siRNAs", Nature, 432(7014):173-178 (2004).

Stirchak, et al., "Uncharged stereoregular nucleic acid analogs. 1. Synthesis of a cytosine-containing oligomer with carbamate internucleoside linkages", Organic Chem., 52:4202, (1987).

Urnov, et al, "Highly efficient endogenous human gene correction using designed zinc-finger nucleases", Nature, 435:646-651 (2005).

Vasquez, et al., "Chromosomal mutations induced by triplex-forming oligonucleotides in mammalian cells", Nucl. Acids Res., 27:1176-1181 (1999).

Vasquez, et al., "Manipulating the mammalian genome by homologous recombination", Proc. Natl. Acad. Sci. USA, 98:8403-8410 (2001).

Wang, et al., "Mutagenesis in mammalian cells induced by triple helix formation and transcription-coupled repair", Science, 271:802-805 (1996).

Wu, et al., "Increased efficiency of oligonucleotide-mediated gene repair through slowing replication fork progression", Proc. Natl. Acad. Sci. USA, 102:2508-2513 (2005).

Zielke, et al., "Repetitive synchronization of human lymphoblast cultures with excess thymidine", Methods Cell Biol., 8:107-121 (1974).

\* cited by examiner

SEQUENCE LISTING

<160> NUMBER OF SEQ ID NOS: 21

<210> SEQ ID NO 1
<211> LENGTH: 10
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to lysine
<220> FEATURE:
<221> NAME/KEY: misc_feature
<222> LOCATION: (1)..(1)
<223> OTHER INFORMATION: 2,6-diaminopurine
<220> FEATURE:
<221> NAME/KEY: misc_feature
<222> LOCATION: (4)..(4)
<223> OTHER INFORMATION: 2,6-diaminopurine
<220> FEATURE:
<221> NAME/KEY: misc_feature
<222> LOCATION: (6)..(6)
<223> OTHER INFORMATION: 6-thiouracil
<220> FEATURE:
<221> NAME/KEY: misc_feature
<222> LOCATION: (8)..(8)
<223> OTHER INFORMATION: 2,6-diaminopurine
<220> FEATURE:
<221> NAME/KEY: misc_feature
<222> LOCATION: (10)..(10)
<223> OTHER INFORMATION: 6-thiouracil
<220> FEATURE:
<221> NAME/KEY: misc_feature
<222> LOCATION: (10)..(10)
<223> OTHER INFORMATION: Linked to lysine

<400> SEQUENCE: 1 ncgncncncn                                                              10

<210> SEQ ID NO 2
<211> LENGTH: 10
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to lysine
<220> FEATURE:
<221> NAME/KEY: misc_feature
<222> LOCATION: (1)..(1)
<223> OTHER INFORMATION: 1,6-diaminopurine
<220> FEATURE:
<221> NAME/KEY: misc_feature
<222> LOCATION: (3)..(3)
<223> OTHER INFORMATION: 6-thiouracil
<220> FEATURE:
<221> NAME/KEY: misc_feature
<222> LOCATION: (5)..(5)
<223> OTHER INFORMATION: 1,6-diaminopurine
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: 6-thiouracil
<220> FEATURE:
<221> NAME/KEY: misc_feature
<222> LOCATION: (10)..(10)
<223> OTHER INFORMATION: Linked to Lysine

```
<400> SEQUENCE: 2 ngngngncgn                                                          10

<210> SEQ ID NO 3
<211> LENGTH: 10
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to lysine
<220> FEATURE:
<221> NAME/KEY: misc_feature
<222> LOCATION: (2)..(2)
<223> OTHER INFORMATION: 6-thiouracil
<220> FEATURE:
<221> NAME/KEY: misc_feature
<222> LOCATION: (3)..(3)
<223> OTHER INFORMATION: 1,6-diaminopurine
<220> FEATURE:
<221> NAME/KEY: misc_feature
<222> LOCATION: (5)..(5)
<223> OTHER INFORMATION: 1,6-diaminopurine
<220> FEATURE:
<221> NAME/KEY: misc_feature
<222> LOCATION: (6)..(6)
<223> OTHER INFORMATION: 6-thiouracil
<220> FEATURE:
<221> NAME/KEY: misc_feature
<222> LOCATION: (8)..(8)
<223> OTHER INFORMATION: 1,6-diaminopurine
<220> FEATURE:
<221> NAME/KEY: misc_feature
<222> LOCATION: (10)..(10)
<223> OTHER INFORMATION: 6-thiouracil
<220> FEATURE:
<221> NAME/KEY: misc_feature
<222> LOCATION: (10)..(10)
<223> OTHER INFORMATION: Linked to lysine

<400> SEQUENCE: 3 gnngnncncn                                                          10

<210> SEQ ID NO 4
<211> LENGTH: 10
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to lysine
<220> FEATURE:
<221> NAME/KEY: misc_feature
<222> LOCATION: (1)..(1)
<223> OTHER INFORMATION: 1,6-diaminopurine
<220> FEATURE:
<221> NAME/KEY: misc_feature
<222> LOCATION: (3)..(3)
<223> OTHER INFORMATION: 6-thiouacil
<220> FEATURE:
<221> NAME/KEY: misc_feature
<222> LOCATION: (5)..(5)
<223> OTHER INFORMATION: 1,6-diaminouracil
<220> FEATURE:
<221> NAME/KEY: misc_feature
<222> LOCATION: (6)..(6)
<223> OTHER INFORMATION: 6-thiouracil
<220> FEATURE:
<221> NAME/KEY: misc_feature
<222> LOCATION: (8)..(8)
<223> OTHER INFORMATION: 6-thiouracil
<220> FEATURE:
```

-continued

```
<221> NAME/KEY: misc_feature
<222> LOCATION: (9)..(9)
<223> OTHER INFORMATION: 1,6-diaminouracil
<220> FEATURE:
<221> NAME/KEY: misc_feature
<222> LOCATION: (10)..(10)
<223> OTHER INFORMATION: Linked to lysine

<400> SEQUENCE: 4 ngngnncnnc                                                              10

<210> SEQ ID NO 5
<211> LENGTH: 20
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(5)
<223> OTHER INFORMATION: pseudoisocytosine
<220> FEATURE:
<221> NAME/KEY: misc_feature
<222> LOCATION: (8)..(9)
<223> OTHER INFORMATION: pseudoisocytosine
<220> FEATURE:
<221> NAME/KEY: misc_feature
<222> LOCATION: (10)..(11)
<223> OTHER INFORMATION: Linked by three 8-amino-2,6-dioxaoctanoic acid
      moleules
<220> FEATURE:
<221> NAME/KEY: misc_feature
<222> LOCATION: (20)..(20)
<223> OTHER INFORMATION: Linked to lys-lys-lys

<400> SEQUENCE: 5
nnnnnttnnt tccttccccc                                                   20

<210> SEQ ID NO 6
<211> LENGTH: 13
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to lysine
<220> FEATURE:
<221> NAME/KEY: misc_feature
<222> LOCATION: (1)..(1)
<223> OTHER INFORMATION: 6-thiouracil
<220> FEATURE:
<221> NAME/KEY: misc_feature
<222> LOCATION: (2)..(2)
<223> OTHER INFORMATION: 1,6-diaminopurine
<220> FEATURE:
<221> NAME/KEY: misc_feature
<222> LOCATION: (3)..(3)
<223> OTHER INFORMATION: 6-thiouracil
<220> FEATURE:
<221> NAME/KEY: misc_feature
<222> LOCATION: (5)..(5)
<223> OTHER INFORMATION: 1,6-diaminopurine
<220> FEATURE:
<221> NAME/KEY: misc_feature
<222> LOCATION: (7)..(7)
<223> OTHER INFORMATION: 1,6-diaminopurine
<220> FEATURE:
<221> NAME/KEY: misc_feature
<222> LOCATION: (8)..(8)
<223> OTHER INFORMATION: 6-thiouracil
<220> FEATURE:
<221> NAME/KEY: misc_feature
<222> LOCATION: (10)..(11)
<223> OTHER INFORMATION: 1,6-diaminopurine
```

```
<220> FEATURE:
<221> NAME/KEY: misc_feature
<222> LOCATION: (13)..(13)
<223> OTHER INFORMATION: 6-thiouracil
<220> FEATURE:
<221> NAME/KEY: misc_feature
<222> LOCATION: (13)..(13)
<223> OTHER INFORMATION: Linked to Lys-lys-lys-lys

<400> SEQUENCE: 6
nnngncnngn ncn                                                             13

<210> SEQ ID NO 7
<211> LENGTH: 13
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to lys
<220> FEATURE:
<221> NAME/KEY: misc_feature
<222> LOCATION: (1)..(1)
<223> OTHER INFORMATION: 1,6-diaminopurine
<220> FEATURE:
<221> NAME/KEY: misc_feature
<222> LOCATION: (3)..(4)
<223> OTHER INFORMATION: 6-thiuracil
<220> FEATURE:
<221> NAME/KEY: misc_feature
<222> LOCATION: (6)..(6)
<223> OTHER INFORMATION: 1,6-diaminopurine
<220> FEATURE:
<221> NAME/KEY: misc_feature
<222> LOCATION: (7)..(7)
<223> OTHER INFORMATION: 6-thiouracil
<220> FEATURE:
<221> NAME/KEY: misc_feature
<222> LOCATION: (9)..(9)
<223> OTHER INFORMATION: 6-thiouracil
<220> FEATURE:
<221> NAME/KEY: misc_feature
<222> LOCATION: (11)..(11)
<223> OTHER INFORMATION: 1,6-diaminopurine
<220> FEATURE:
<221> NAME/KEY: misc_feature
<222> LOCATION: (12)..(12)
<223> OTHER INFORMATION: 6-thiouracil
<220> FEATURE:
<221> NAME/KEY: misc_feature
<222> LOCATION: (13)..(13)
<223> OTHER INFORMATION: 1,6-diaminopurine
<220> FEATURE:
<221> NAME/KEY: misc_feature
<222> LOCATION: (13)..(13)
<223> OTHER INFORMATION: Linked to Lys-lys-lys-lys

<400> SEQUENCE: 7
ngnncnngnc nnn                                                             13

<210> SEQ ID NO 8
<211> LENGTH: 13
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to Lys
<220> FEATURE:
<221> NAME/KEY: misc_feature
<222> LOCATION: (13)..(13)
<223> OTHER INFORMATION: Linked to Lys-lys-lys-lys
```

<400> SEQUENCE: 8
tatgacatga act                                                     13

<210> SEQ ID NO 9
<211> LENGTH: 13
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to Lys
<220> FEATURE:
<221> NAME/KEY: misc_feature
<222> LOCATION: (13)..(13)
<223> OTHER INFORMATION: Linked to Lys-Lys-Lys-Lys

<400> SEQUENCE: 9
agttcatgtc ata                                                     13

<210> SEQ ID NO 10
<211> LENGTH: 30
<212> TYPE: DNA
<213> ORGANISM: Artificial Sequence
<220> FEATURE:
<223> OTHER INFORMATION: Synthetic peptide nucleic acid

<400> SEQUENCE: 10
aggaaggggg gggtggtggg ggaggggggag                                  30

<210> SEQ ID NO 11
<211> LENGTH: 30
<212> TYPE: DNA
<213> ORGANISM: Artificial Sequence
<220> FEATURE:
<223> OTHER INFORMATION: Synthetic peptide nucleic acid

<400> SEQUENCE: 11
ggaggagtgg aggggagtga gggggggggg                                   30

<210> SEQ ID NO 12
<211> LENGTH: 51
<212> TYPE: DNA
<213> ORGANISM: Artificial Sequence
<220> FEATURE:
<223> OTHER INFORMATION: Synthetic peptide nucleic acid

<400> SEQUENCE: 12
ttcgaacctt cgaagtcgat gacgggagat ttagagtctg ctcccctttgg c           51

<210> SEQ ID NO 13
<211> LENGTH: 40
<212> TYPE: DNA
<213> ORGANISM: Artificial Sequence
<220> FEATURE:
<223> OTHER INFORMATION: Synthetic peptide nucleic acid

<400> SEQUENCE: 13
agggagcaga ctctaaatct gccgtcatcg acttcgaagg                        40

<210> SEQ ID NO 14
<211> LENGTH: 51
<212> TYPE: DNA
<213> ORGANISM: Artificial Sequence
<220> FEATURE:
<223> OTHER INFORMATION: Synthetic peptide nucleic acid

```
<400> SEQUENCE: 14
gttcagcgtg tccggcgagg gcgaggtgag tctatgggac ccttgatgtt t          51

<210> SEQ ID NO 15
<211> LENGTH: 50
<212> TYPE: DNA
<213> ORGANISM: Artificial Sequence
<220> FEATURE:
<223> OTHER INFORMATION: Synthetic peptide nucleic acid

<400> SEQUENCE: 15
aaacatcaag ggtcccatag gtctattctg aagttctcag gatccacgtg            50

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleoride

<400> SEQUENCE: 16
gatcatggtt aagttcatgt cata                                        24

<210> SEQ ID NO 17
<211> LENGTH: 24
<212> TYPE: DNA
<213> ORGANISM: Artificial Sequennce
<220> FEATURE:
<223> OTHER INFORMATION: Synthetic oligonucleoride

<400> SEQUENCE: 17
aatttatgac atgaacttaa ccat                                        24

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18
agcaagggcg aggagctgtt cacc                                        24

<210> SEQ ID NO 19
<211> LENGTH: 23
<212> TYPE: DNA
<213> ORGANISM: Artificial sequence
<220> FEATURE:
<223> OTHER INFORMATION: Synthetic primer

<400> SEQUENCE: 19
cactgcacgc cgtaggtcag ggt                                         23

<210> SEQ ID NO 20
<211> LENGTH: 13
<212> TYPE: DNA
<213> ORGANISM: Unknown
<220> FEATURE:
<223> OTHER INFORMATION: pcNA6 DNA donor

<400> SEQUENCE: 20
agttcatgtc ata                                                    13

<210> SEQ ID NO 21
<211> LENGTH: 13
```

```
<212> TYPE: DNA
<213> ORGANISM: Unknown
<220> FEATURE:
<223> OTHER INFORMATION: pcNA7 DNA donor

<400> SEQUENCE: 21
tcaagtacag tat                                                    13
```

PSEUDOCOMPLEMENTARY OLIGONUCLEOTIDES FOR TARGETED GENE THERAPY

CROSS-REFERENCE TO RELATED APPLICATIONS

This application claims priority under 35 U.S.C. 119 to U.S. Ser. No. 61/165,715 filed Apr. 1, 2009.

STATEMENT REGARDING FEDERALLY FUNDED RESEARCH

The Federal Government has certain rights in this invention by virtue of Grant Nos. R01CA64186 and RO1HL082655 from the National Institute of Health to Peter M. Glazer.

FIELD OF THE INVENTION

The present application is generally related to pseudocomplementary oligonucleotides and their use for targeted gene therapy.

BACKGROUND OF THE INVENTION

Gene targeting via homologous recombination (HR) offers a potential strategy for gene correction. Several groups have shown that gene correction at a chromosomal locus can be mediated by donor DNA fragments that are designed to be homologous to the target gene (differing only at the base pair (bp) of the mutation to be corrected) (Hu, et al., *Mol. Biotech.*, 29:197-210 (2005); Olsen, et al., *J. Gene Med.*, 7:1534-1544 (2005)). Other studies have shown that site-specific chromosomal damage can substantially increase the frequency of FIR by exogenous DNA (Jasin, M., *Trends Genet.*, 12:224-228 (1996)).

One method to create site-specific DNA damage is the use of triplex-forming oligonucleotides (TFOs) which bind as third strands to homopurine/homopyrimidine sites in duplex DNA in a sequence-specific manner (Vasquez, et al., *Nucleic Acids Res.*, 27:1176-1181 (1999)). The formation of a triple helix creates a helical distortion that has been shown to provoke DNA repair and recombination (Vasquez, et al., *Proc. Natl. Acad. Sci. USA*, 98:8403-8410 (2001); Wang, et al., *Science*, 271:802-805 (1996); Dana, et al., *J. Biol. Chem.*, 276:18018-18023 (2001)). This approach has been used successfully to stimulate targeted recombination at chromosomal loci in mammalian cells, with recombination frequencies of up to 0.2%. Similarly, another class of DNA-binding molecules, bis-peptide nucleic acids (bis-PNAs), which can bind to homopurine regions to form PNA/DNA/PNA triplexes with a displaced DNA strand, can create PNA 'clamps' that also create a helical distortion that strongly provokes repair and recombination (Rogers, et al., *Proc. Natl. Acad. Sci. USA*, 99:16695-16700 (2002)).

However, both of these approaches are limited by the requirement for a polypurine sequence in the target duplex to enable triplex formation. To overcome this limitation, Lohse et al. *Proc. Nad., Acad. Sci. USA*, 96:11804-11808 (1999) reported the design of pseudo-complementary PNAs (pcPNAs), which can bind to duplex DNA at mixed purine-pyrimidine sequences via double duplex strand invasion to form four stranded complexes. To achieve pseudo-complementarity, pePNAs were synthesized with 2,6-diaminopurine (D) and 2-thiouracil (sU) nucleobases instead of As and Ts, respectively, apart from natural guanine and cytosine bases. While D and sU substitutions impede the base pairing between two mutually pseudocomplementary PNA oligomers due to steric hindrance, they do not prevent pcPNAs from binding to the corresponding sequences in DNA carrying natural nucleobases. As a result, a pair of pcPNAs can pry open a duplex DNA site via formation of double-duplex invasion complexes. This mode of pcPNA-mediated DNA recognition substantially extends the range of possible DNA targets for pcPNAs, since almost any chosen mixed-base site in duplex DNA can be targeted with pcPNAs (A+T content$\leq$40%).

Recognition of duplex DNA at mixed sequence sites has been achieved by only two other classes of DNA binding molecules, polyamides (Home, et al., *J. Am. Chem. Soc.*, 112:2435-2437 (1990)) and modular zinc finger polypeptides (Umov, et al, *Nature*, 435:646-651 (2005)). Polyamides show high affinity for duplex DNA in the minor groove, but they have not shown the ability to mediate targeted genome modification in cells. Zinc finger polypeptides, when linked to nuclease domains to form zinc finger nucleases (ZFNs), can induce recombination events in mammalian cells via the direct creation of double strand breaks, which promote recombination (Urnov, et al, *Nature*, 435:646-651 (2005)). Frequencies of gene modification achieved with ZFNs (plus donor DNAs) appear to be high, however, they are complex proteins that must be expressed in cells from viral or plasmid vectors, which can also produce variable levels of non-specific, off-target nuclease activity.

pcPNAs, in contrast, are relatively simple, chemically-synthesized oligomers which appear to have favorable toxicity profiles. It has been reported that pcPNAs can block access of T7 RNA polymerase to the corresponding promoter site in vitro thereby inhibiting transcription initiation (Lohse, et al., *Proc. Natl. Acad. Sci. USA*, 96:11804-11808 (1999)). It has also been shown that a pair of psoralen-conjugated pcPNAs can direct the formation of targeted psoralen photoadducts on duplex plasmid DNA in vitro (Kim, et al., *Bioconjug. Chem.*, 18:567-572 (2007)) as well as at a chromosomal site in living cells, leading to the production of site-specific mutations with high efficiency and specificity (Kim, et al., *Nucleic Acids*, 35:7604-7613 (2007)).

To effectively correct human disease-related genes, there exists a need to improve the naturally low level of homologous recombination at chromosomal sites in human cells.

Therefore, it is an object of the invention provide recombinagenic or mutagenic compositions including a pair of pseudocomplementary oligonucleotides having sequences that form a double duplex nucleic acid molecule with a target sequence of a double-stranded nucleic acid molecule, and a donor oligonucleotide essentially complementary to a recombination target sequence of the double-stranded nucleic acid molecule, and methods for their use.

It is a further object of the invention to provide recombinagenic or mutagenic compositions having higher percentages of recombination.

SUMMARY OF THE INVENTION

Compositions and methods for targeted gene therapy are disclosed. Compositions containing molecules, referred to as "double duplex-forming molecules," that bind to duplex DNA in a sequence-specific manner to form a four-stranded structure. It has been discovered that double duplex-forming molecules, such as a pair of pseudocomplementary oligonucleotides, can induce recombination with a donor oligonucleotide at a chromosomal site in mammalian cells. Pseudocomplementary oligonucleotides are complementary oligonucleotides that contain one or more modifications such that they do not recognize or hybridize to each other, for example due to steric hindrance, but each can recognize and hybridize to its complementary nucleic acid strands at the target site. Preferred pseudocomplementary oligonucleotides include Pseudocomplementary peptide nucleic acids (pcP-NAs). This strategy is more efficient and provides increased flexibility over other methods of induced recombination such as triple-helix oligonucleotides and bis-peptide nucleic acids which require a polypurine sequence in the target double-stranded DNA. The design ensures that the pseudocomplementary oligonucleotides do not pair with each other but instead bind the cognate nucleic acids at the target site, inducing the formation of a double duplex.

The double duplex-forming pseudocomplementary oligonucleotides are administered to a patient in need thereof in combination with a donor oligonucleotide that is essentially homologous to the target sequence in need of repair or replacement. By activating cellular mechanisms involved in DNA synthesis, repair and recombination, the double duplex-forming pseudocomplementary oligonucleotides can introduce one or more mutations at a site of interest by increasing the efficiency of targeted recombination of the donor oligonucleotide. The mutation may activate, inactivate, or otherwise alter the activity and function of the target gene. The induction of targeted recombination can be used to correct a mutation in a target gene that is the cause of a genetic disorder, such as by converting the DNA sequence of the target gene to the normal native sequence. Alternatively, if the target gene is a viral gene needed for viral survival or reproduction or an oncogene causing unregulated proliferation, such as in a cancer cell, then the use of recombinagenic pseudocomplementary oligonucleotides and donor oligonucleotides is useful for inducing a mutation or correcting the mutation, thereby inactivating the gene to incapacitate or prevent reproduction of the virus or to terminate or reduce the uncontrolled proliferation of the cancer cell.

The pseudocomplementary oligonucleotides/donor oligonucleotide compositions may be administered in combination with a second therapeutic agent that enhances access of the pseudocomplementary oligonucleotides and/or the donor oligonucleotide to the target site, such a histone deacetylase (HDAC) inhibitor, an agent that enhances or increases the nucleotide excision repair pathway, or an agent that enhances uptake or delivery of the oligonucleotides (such as the lysosomotropic agent chloroquine).

DETAILED DESCRIPTION OF THE INVENTION

It has been discovered that a pair of pseudocomplementary oligonucleotides can be used to stimulate recombination of donor oligonucleotide at a chromosomal site in mammalian cells. As described in detail in the examples below, pseudocomplementary oligonucleotide-mediated recombination was significantly greater than expected as compared to other methods of DNA molecule binding-induced recombination, such as triplex-forming oligonucleotides (TFOs) and bis-PNA's. The activity of the pseudocomplementary oligonucleotides and donor DNAs in gene correction can be further enhanced by measures to modify target site accessibility and to improve oligomer delivery.

I. Compositions

Figure 1:
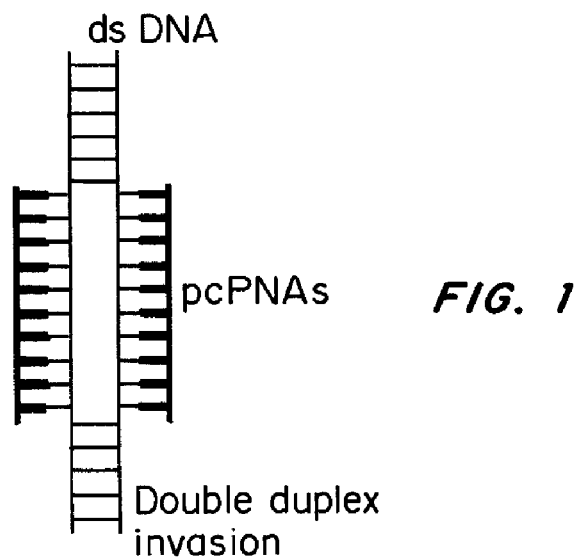
FIG. 1 is diagram of the double duplex strand invasion complex formed by a pair of pcPNAs on complementary double stranded DNA.

Disclosed herein are compositions containing molecules, referred to as "double duplex-forming molecules", that bind to duplex DNA in a sequence-specific manner to form a four-stranded structure, such as the one depicted in FIG. 1.

The double duplex-forming molecules can be used to induce site-specific homologous recombination in mammalian cells when combined with donor DNA molecules. The donor DNA molecules can contain mutated nucleic acids relative to the target DNA sequence. This is useful to activate, inactivate, or otherwise alter the function of a polypeptide or protein encoded by the targeted duplex DNA. Double duplex-forming molecules include triplex-forming oligonucleotides and peptide nucleic acids.

A. Double Duplex-forming Oligonucleotides

As used herein, an "oligonucleotide" or a "polynucleotide" is a synthetic or isolated nucleic acid polymer comprising a plurality of nucleotide subunits of defined base sequence. As used herein, a "pseudocomplementary oligonucleotides" refers to a pair of complementary oligonucleotides that contain one or more modifications such that they do not recognize or hybridize to each other, for example due to steric hindrance, but each can recognize and hybridize to its complementary nucleic acid strands at the target site. This design ensures that the pseudocomplementary oligonucleotides do not pair with each other but instead bind the cognate nucleic acids at the target site, inducing the formation of a double duplex such as the one shown in FIG. 1. In a preferred embodiment the double duplex-forming molecules are pseudocomplementary oligonucleotides.

1. Heterocyclic Bases

Figure 2:
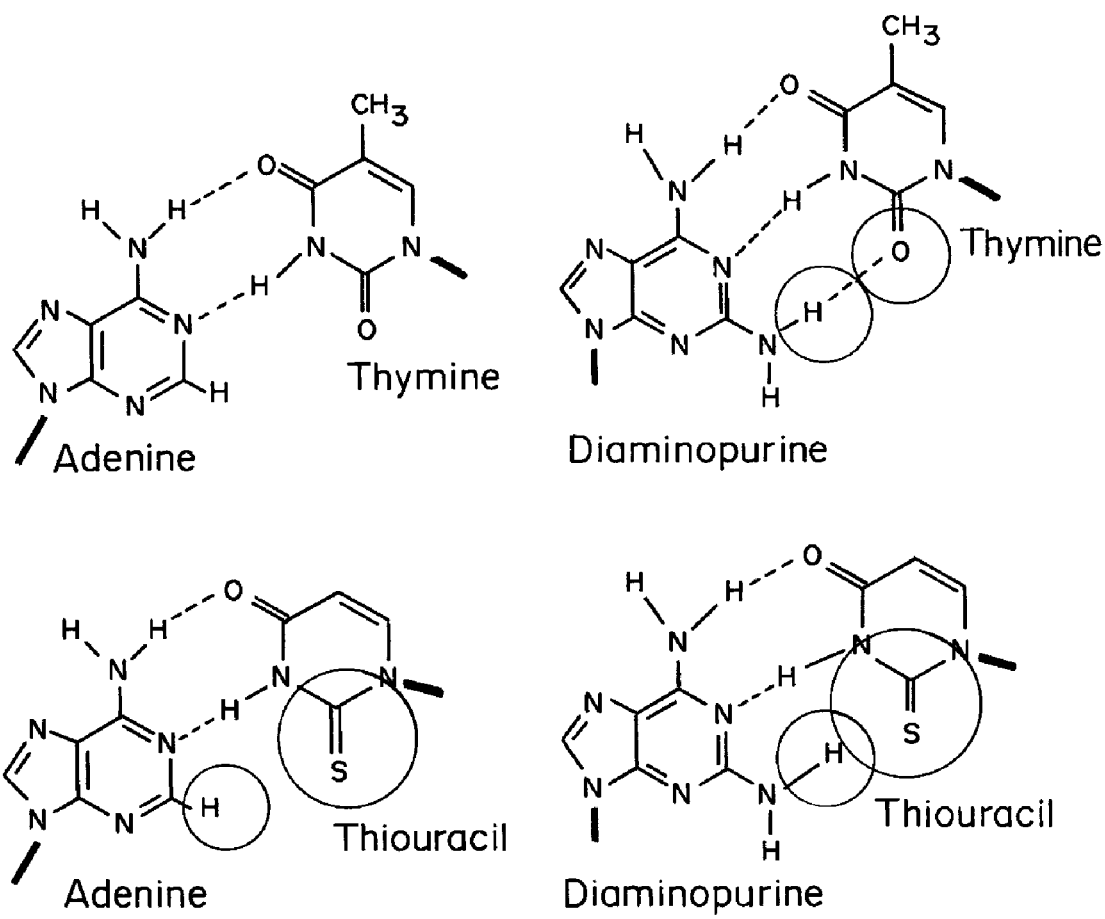
FIG. 2 shows the structure and base pairing between 2,6-diaminopurine:thymine and between adenine:2-thiouracil in comparison to the canonical A:T base pair. Steric hindrance prevents similar base pairing between 2,6-diaminopurine and 2-thiouracil.

In preferred embodiments a pair of pseudocomplementary oligonucleotides are generated by replacing one or more of the standard heterocyclic nucleic acid bases (uracil, thymine, cytosine, adenine and guanine) with any suitable base analog that that will allow each pseudocomplementary oligonucleotide to recognize and bind or hybridize to its complementary strand at the target site, but not to each other. Examples of suitable base analogs that can be used to generate pseudocomplementary oligonucleotides are known in the art, for example 2,6-diaminopurine (D) and 2-thiouracil, as shown in FIG. 2, can be used instead of adenine and thymine, respectively. A number of destabilizing guanine and cytosine base analogs including 7-ethyl-7-deazaguanine (EtcG) and N4-ethylcytosine (EtC), 6-thioguanine (sG), 5-nitrocytosine (NitroC), 2-pyrimidinone (P; the free base of zebularine) and 6-methylfuranopyrimidinone (MefP) have also been evaluated for pseudocomplementary properties (Lahoud, et al., *Nucleic Acids Research*, 36(22):6999-7008 (2008)). Substitution of base analogs to generate pseudocomplementary oligonucleotides should not prevent the oligonucleotides from binding with high specificity to the target site.

2. Sugars

Double duplex-forming oligonucleotides can be constructed with conventional ribose and deoxyribose sugars and conventional stereoisomers, but also other sugars, including L enantiomers and alpha anomers. The sugar moiety of the oligonucleotides can be a sugar analog, or include modifications on the sugar moiety, e.g., wherein one or more of the hydroxyl groups are replaced with halogen atoms or aliphatic groups, or are functionalized as ethers, amines, or the like. Sugar moiety modifications include, but are not limited to, 2'-β-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O-(N-(methyl)acetamido) (2'-OMA).

Locked nucleic acids (LNA) are modified RNA nucleotides (see, for example, Braasch, et al., *Chem. Biol.,* 8(1):1-7 (2001)). LNAs form hybrids with DNA which are at least as stable as peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs. Substitution of sugar analogs to generate pseudocomplementary oligonucleotides should not prevent the oligonucleotides from binding with high specificity to the target site.

3. Backbone

The nucleotide subunits of the oligonucleotide are connected by an internucleotide bond that refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group, such as phosphite, phosphonate, H-phosphonate, phosphoramidate, phosphorothioate, and/or phosphorodithioate linkages. Oligonucleotides containing phosphorothioate internucleotide linkages have been shown to be more stable in vivo. Modified internucleotide linkages also include phosphate analogs, analogs having achiral and uncharged intersubunit linkages (e.g., Sterchak, E. P. et al., *Organic Chem.,* 52:4202, (1987)), and uncharged morpholino-based polymers having achiral intersubunit linkages (see, e.g., U.S. Pat. No. 5,034,506). Some internucleotide linkage analogs include morpholidate, acetal, and polyamide-linked heterocycles.

Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. Therefore, each PNA nucleotide typically comprises a heterocyclic base (nucleic acid base), a sugar moiety attached to the heterocyclic base, and a N-(2-aminoethyl)-glycine. The various heterocyclic bases are linked to the backbone by methylene carbonyl bonds, which allow them to form PNA-DNA or PNA-RNA duplexes via Watson-Crick base pairing with high affinity and sequence-specificity. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications, particularly those relating to PNAs, include peptide and amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), amino acids such as lysine particularly useful if positive charges are desired in the PNA, and the like. Methods for the chemical assembly of PNAs are well known (See: U.S. Pat. Nos. 5,539,082, 5,527,675, 5,623,049, 5,714,331, 5,736,336, 5,773,571 or 5,786,571 which are incorporated herein by reference). Backbone modifications used to generate pseudocomplementary oligonucleotides should not prevent the oligonucleotides from binding with high specificity to the target site.

In one embodiment, the pseudocomplementary oligonucleotides are pseudocomplementary peptide nucleic acids (pcPNAs). Izvolsky, et al., have reported that pcPNAs containing as few as eight nucleobases can form stable and sequence-specific complexes with duplex DNA in a very salt-dependent manner (Izvolsky, et al., *Biochemistry,* 10908-10913 (2000)). pcPNAs may optionally include one or more terminal amino acids to increase stability, affinity of the pcP- NAs for DNA, or increase solubility of pcPNAs. Commonly used positively charged moieties include the amino acids lysine and arginine, although other positively charged moieties may also be useful. For example, lysine and arginine residues can be added to the carboxy terminus of a PNA strand. As illustrated in the examples below, in a preferred embodiment, pcPNAs are synthesized with 2,6-diaminopurine (D) and 2-thiouracil instead of adenine and thymine, respectively, which prevent binding between the complementary pair of pcPNA's, but allow the pcPNA's to bind specifically to the DNA target site and facilitate stand invasion and double duplex formation (FIGS. 1 and 2).

Oligonucleotides may further be modified to be end capped to prevent degradation using a 3' propylamine group. Procedures for 3' or 5' capping oligonucleotides are well known in the art.

4. Double Duplex Target Sequence

The predetermined region that the double duplex-forming molecules bind to is a target region referred to herein as the "double duplex target sequence", "double duplex target region", or "double duplex target site". The double duplex target sequence (DDTS) for the double duplex-forming oligonucleotides disclosed herein for example, can be within or adjacent to a human gene in need of induced gene correction. The DDTS can be within the coding DNA sequence of the gene or within introns. The DDTS can also be within DNA sequences which regulate expression of the target gene, including promoter or enhancer sequences.

The nucleotide sequence of the pseudocomplementary oligonucleotides is selected based on the sequence of the DDTS. Therapeutic administration of pseudocomplementary oligonucleotides involves two single stranded oligonucleotides added to double stranded DNA. One pseudocomplementary oligonucleotide strand is complementary to the DDTS, while the other is complementary to the displaced DNA strand. The use of pseudocomplementary oligonucleotides, particularly pcPNAs are not subject to limitation on sequence choice and/or target length and specificity as are triplex-forming oligonucleotides, helix-invading peptide nucleic acids (bis-PNAs) and side-by-side minor groove binders. Pseudocomplementary oligonucleotides do not require third-strand Hoogsteen-binding, and therefore are not restricted to homopurine targets. Pseudocomplementary oligonucleotides can be designed for mixed, general sequence recognition of a desired target site. Preferably, the target site contains an A:T base pair content of about 40% or greater. Preferably pseudocomplementary oligonucleotides are between about 8 and 50 nucleobases, more preferably 8 to 30, even more preferably between about 8 and 20 nucleobases.

The pseudocomplementary oligonucleotides should be designed to bind to the target site (DDTS) at a distance of between about 1 to 800 bases from the target site of the donor oligonucleotide. More preferably, the pseudocomplementary oligonucleotides bind at a distance of between about 25 and 75 bases from the donor oligonucleotide. Most preferably, the pseudocomplementary oligonucleotides bind at a distance of about 50 bases from the donor oligonucleotide. Preferred pcPNA sequences for targeted repair of a mutation in the β-globin intron IVS2 (G to A) are described in the examples below.

Preferably, the pseudocomplementary oligonucleotides bind/hybridize to the target nucleic acid molecule under conditions of high stringency and specificity. Most preferably, the oligonucleotides bind in a sequence-specific manner and induce the formation of double duplex. Specificity and binding affinity of the pseudocomplimetary oligonucleotides may vary from oligonucleotide to oligonucleotide, depending on factors such as oligonucleotide length, the number of G:C and A:T base pairs, and the formulation.

As used herein, an oligonucleotide is said to be substantially complementary to a target region when the oligonucleotide has a base composition which allows for the formation of a double duplex with the target region. As such, an oligonucleotide is substantially complementary to a target region even when there are non-complementary bases present in the oligonucleotide.

B. Donor Oligonucleotides

The double duplex-forming pseudocomplementary oligonucleotides are administered in combination with a donor oligonucleotide that is homologous to the target sequence in need of repair or replacement (except for one or several by that are to be corrected or modified). Donor oligonucleotides are also referred to herein as donor fragments, donor nucleic acids, donor DNA, or donor DNA fragments. Donor fragments may range in length from 20 nucleotides to several thousand. This strategy is intended to increase the probability of recombination with the homologous donor DNA. It is understood in the art that a greater number of homologous nucleotides within the donor fragment tends to increase the probability that the donor fragment will be recombined into a target region, or target site, collectively referred to herein as the recombination target sequence (RTS). However, donor DNAs that are single-stranded and of length 20 to 100 nucleotides are preferred. As demonstrated in the examples that follow, pseudocomplementary oligonucleotides administered in combination with a donor oligonucleotide effectively induce homologous recombination of the donor oligonucleotide at the RTS. The term "recombinagenic" as used herein, is used to define a DNA fragment, oligonucleotide, or composition as being able to recombine into a target site or sequence or induce recombination of another DNA fragment, oligonucleotide, or composition. As further demonstrated by the examples below, the use of pseudocomplementary oligonucleotides was more effective than use of triplex-forming oligonucleotides or bis-PNA for targeted recombination. These results were unexpected.

The RTS for donor oligonucleotides disclosed herein can be within or adjacent to a human gene in need of induced gene correction. The RTS can be within the coding DNA sequence of the gene or within introns. The RTS can also be within DNA sequences which regulate expression of the target gene, including promoter or enhancer sequences.

Donor fragments may range in length from 30 nucleotides to several thousand. It is preferable that the donor oligonucleotide is at least 10 nucleotides in length. It is more preferable that the oligonucleotide be at least 20 nucleotides in length. In a preferred embodiment the donor oligonucleotide is between about 25 and 75 nucleobases. In the most preferred embodiment the donor oligonucleotide is about 50 nucleobases in length. The donor oligonucleotide can exist in single stranded or double stranded form, but is preferably administered as a single strand. Donor oligonucleotides are preferably DNA oligonucleotides, composed of the principal naturally-occurring nucleotides (uracil, thymine, cytosine, adenine and guanine) as the heterocyclic bases, deoxyribose as the sugar moiety, and phosphate ester linkages. Donor oligonucleotides may include modifications to nucleobases, sugar moieties, or backbone/linkages, as described above, depending on the desired structure of the replacement sequence at the site of recombination or to provide some resistance to degradation by nucleases. Modifications to the donor oligonucleotide should not prevent the donor oligonucleotide from successfully recombining at the recombination target sequence in the presence of pseudocomplementary oligonucleotides.

C. Oligonucleotide Fusions

Formulations of the oligonucleotides embrace fusions of the oligonucleotides or modifications of the oligonucleotides, wherein the oligonucleotide is fused to another moiety or moieties, e.g., targeting moiety or another therapeutic agent. Such analogs may exhibit improved properties such as increased cell membrane permeability, activity and/or stability. Examples of moieties which may be linked or unlinked to the oligonucleotides include, for example, targeting moieties which provide for the delivery of oligonucleotides to specific cells, e.g., antibodies to blood-forming cells, immune cells, lung cells or any other preferred cell type, as well as receptor and ligands expressed on the preferred cell type. Preferably, the moieties target red blood cell-forming cells. Other moieties that may be provided with the oligonucleotides include protein transduction domains (PTDs), which are short basic peptide sequences present in many cellular and viral proteins that mediate translocation across cellular membranes. Example protein transduction domains that are well-known in the art include the Antennapedia PTD and the TAT (trans-activator of transcription) PTD.

II. Methods of Treatment and Prevention

The pseudocomplementary oligonucleotides are used to stimulate homologous recombination of an exogenously supplied, donor oligonucleotide, into a target region. Double duplex-forming pseudocomplementary oligonucleotides bind/hybridize to a target sequence within a target gene or target region of a chromosome, forming a double duplex region. By activating cellular mechanisms involved in DNA synthesis, repair and recombination, the double duplex-forming pseudocomplementary oligonucleotides can introduce one or more mutations at a site of interest by increasing the efficiency of targeted recombination of the donor oligonucleotide. The mutation generated activates, inactivates, or alters the activity and function of the target gene.

In targeted recombination, double duplex-forming pseudocomplementary oligonucleotides are administered to a cell in combination with a separate oligonucleotide referred to herein as donor fragment, which minimally contains a sequence complementary to the region targeted for recombination. The donor sequence can contain a nucleic acid sequence alteration, as referred to herein as a mutation, region targeted for recombination, for example, a substitution, a deletion, or an insertion of one or more nucleotides. Successful recombination of the donor sequence results in a change of the sequence of the target region. The co-administration of double duplex-forming pseudocomplementary oligonucleotides with the donor fragment increases the frequency of recombination of the donor fragment within the targeted region targeted when compared to procedures which do not employ double duplex-forming pseudocomplementary oligonucleotides.

The induction of targeted recombination may be best served, for example, to correct a mutation in a target gene that is the cause of a genetic disorder. If the target gene contains a mutation that is the cause of a genetic disorder, then the pseudocomplementary oligonucleotides are useful for repair by recombination of the donor sequence that restores the DNA sequence of the target gene to normal. Alternatively, if the target gene is a viral gene needed for viral survival or reproduction or an oncogene causing unregulated proliferation, such as in a cancer cell, then the use of recombinagenic pseudocomplementary oligonucleotides should be useful for inducing a mutation or correcting the mutation, by homologous recombination, thereby inactivating the gene to incapacitate or prevent reproduction of the virus or to terminate or reduce the uncontrolled proliferation of the cancer cell.

A. Combination Therapies

The pseudocomplementary oligonucleotides can be used alone or in combination with other agents. As used herein, two agents are said to be used in combination when the two agents are co-administered, or when the two agents are administered in a fashion so that both agents are present within the cell or serum simultaneously. The pseudocomplementary oligonucleotides/donor oligonucleotide compositions may be administered in combination with a second therapeutic agent that is commonly used in the treatment of a particular disease or disorder to be treated. Preferably, the compositions are administered in combination with an agent that enhances access of the pseudocomplementary oligonucleotides and/or the donor oligonucleotide to the target site. For example, the disclosed compositions can be administered in combination with a histone deacetylase (HDAC) inhibitor, such as suberoylanilide hydroxamic acid (SAHA). As described in the examples below, administration of the disclosed compositions in combination with SAHA enhanced gene correction frequencies. The examples below also demonstrate that the nucleotide excision repair pathway participates in pcPNA-mediated recombination. Therefore, the disclosed compositions can be administered in combination with an agent that enhances or increases the nucleotide excision repair pathway, for example an agent that increases the expression, or activity, or localization to the target site, of the endogenous damage recognition factor XPA. Compositions may also be administered in combination with a second active agent that enhances uptake or delivery of the oligonucleotides. For example, the lysosomotropic agent chloroquine has been shown to enhance delivery of pcPNAs.

R. Conditions to be Treated

The relevance of DNA repair and mediated recombination as gene therapy is apparent when studied in the context of human genetic diseases. Suitable genetic diseases that can be treated using the disclosed methods include, but are not limited to, cystic fibrosis, hemophelia, globinopathies such as sickle cell anemia and beta-thalassemia. If the target gene contains a mutation that is the cause of a genetic disorder, then pseudocomplementary oligonucleotides administered in combination with a donor oligonucleotide is useful for mutagenic repair that may restore the DNA sequence of the target gene to normal.

Targeted DNA repair and recombination induced by double duplex-forming pseudocomplementary oligonucleotides is especially useful to treat genetic deficiencies, disorders and diseases caused by mutations in single genes. Pseudocomplementary oligonucleotides are also especially useful to correct genetic deficiencies, disorders and diseases caused by point mutations.

Worldwide, globinopathies account for significant morbidity and mortality. Over 1,200 different known genetic mutations affect the DNA sequence of the human alpha-like (HBZ, HBA2, HBA 1, and HBQ1) and beta-like (HBE1, HBGI, HBD, and HBB) globin genes. Two of the more prevalent and well-studied globinopathies are sickle cell anemia and β-thalassemia. Substitution of valine for glutamic acid at position 6 of the β-globin chain in patients with sickle cell anemia predisposes to hemoglobin polymerization, leading to sickle cell rigidity and vasoocclusion with resulting tissue and organ damage. In patients with β-thalassemia, a variety of mutational mechanisms results in reduced synthesis of β-globin leading to accumulation of aggregates of unpaired, insoluble α-chains that cause ineffective erythropoiesis, accelerated red cell destruction, and severe anemia.

All together, globinopathies represent the most common single-gene disorders in man. Pseudocomplementary oligonucleotide-mediated recombination is particularly well suited to treat globinopathies, as they are single gene disorders caused by point mutations. The examples that follow demonstrate that the pseudocomplementary oligonucleotide compositions disclosed herein are effective at binding to the human β-globin in living cells. The examples further demonstrate using a reporter based system in living cells, that pseudocomplementary oligonucleotides targeted to specific target sites in the human β-globin gene effectively induce repair of known mutations when co-administered with appropriate donor oligonucleotides.

If the target gene is an oncogene causing unregulated proliferation, such as in a cancer cell, then the donor oligonucleotide is useful for causing a mutation that inactivates the gene and terminates or reduces the uncontrolled proliferation of the cell. The donor oligonucleotide is also a useful anti-cancer agent for activating a repressor gene that has lost its ability to repress proliferation.

The donor oligonucleotide is useful as an antiviral agent when the oligonucleotide is specific for a portion of a viral genome necessary for proper proliferation or function of the virus.

C. Formulations

The disclosed double duplex-forming pseudocomplimentary oligonucleotides and donor fragment compositions are preferably employed for therapeutic uses in combination with a suitable pharmaceutical carrier. Such compositions include an effective amount of pseudocomplimentary oligonucleotides and donor fragment, and a pharmaceutically acceptable carrier or excipient. An effective amount of pseudocomplimentary oligonucleotides may be enough oligonucleotides to induce formation of double-duplex at the target site. An effective amount of pseudocomplimentary oligonucleotides may also be an amount effective to increase the rate of recombination of a donor fragment relative to administration of the donor fragment in the absence of pseudocomplementary oligonucleotides. Compositions should include an amount of donor fragment effective to recombine at the target site in the presence of pseudocomplementary oligonucleotides. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids.

It is understood by one of ordinary skill in the art that nucleotides administered in vivo are taken up and distributed to cells and tissues (Huang, et al., *FEBS Lett.*, 558(1-3):69-73 (2004)). For example, Nyce, et al. have shown that antisense oligodeoxynucleotides (ODNs) when inhaled bind to endogenous surfactant (a lipid produced by lung cells) and are taken up by lung cells without a need for additional carrier lipids (Nyce, et al., *Nature,* 385:721-725 (1997)). Small nucleic acids are readily taken up into T24 bladder carcinoma tissue culture cells (Ma, et al., *Antisense Nucleic Acid Drug Dev.,* 8:415-426 (1998)).

The disclosed compositions including pseudocomplementary oligonucleotides and donor fragments may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles, nanoparticles, or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example, in Sambrook et al., *Molecular Cloning: A Laboratory Manual,* Cold Spring Harbor Laboratory, New York (1989); and Ausubel et al., *Current Protocols in Molecular Biology,* John Wiley & Sons, New York (1994). Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. The nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, optionally with an added preservative. The compositions may take such forms as sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil including synthetic mono- or di-glycerides may be employed. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The oligonucleotides alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and air. For administration by inhalation, the compounds are delivered in the form of an aerosol spray presentation from pressurized packs or a nebulizer, with the use of a suitable propellant.

In some embodiments, the oligonucleotides described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the oligonucleotides are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.*, 14(19):4975-4977 (2004)) and in vivo (Soutsehek, et al., *Nature*, 432 (7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.*, 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe(II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also describes methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

D. Methods of Administration

In general, methods of administering compounds, including oligonucleotides and related molecules, are well known in the art. In particular, the routes of administration already in use for nucleic acid therapeutics, along with formulations in current use, provide preferred routes of administration and formulation for the oligonucleotides described above. Preferably the oligonucleotides are injected into the organism undergoing genetic manipulation, such as an animal requiring gene therapy or anti-viral therapeutics.

The disclosed compositions including pseudocomplementary oligonucleotides and a donor oligonucleotide can be administered by a number of routes including, but not limited to: oral, intravenous, intraperitoneal, intramuscular, transdermal, subcutaneous, topical, sublingual, or rectal means. The preferred route of administration is intravenous. Oligonucleotides can also be administered via liposomes. Such administration routes and appropriate formulations are generally known to those of skill in the art.

Administration of the formulations may be accomplished by any acceptable method which allows the double duplex-forming oligonucleotides and a donor nucleotide, to reach their targets.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The oligonucleotides may be delivered in a manner which enables tissue-specific uptake of the agent and/or nucleotide delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the double duplex-forming oligonucleotides, and donor oligonucleotides, over a certain time period, for example, hours, days, weeks, months or years. This may be accomplished, for example, by repeated administrations of a formulation or by a sustained or controlled release delivery system in which the oliogonucleotides are delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include non-polymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the oligonucleotides are contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos.

3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the oligonucleotides. In addition, a pump-based hardware delivery system may be used to deliver one or more embodiments.

Examples of systems in which release occurs in bursts include systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Compositions including double duplex-forming pseudocomplementary oligonucleotides and donor oligonucleotides and methods of their use will be further understood in view of the following non-limiting examples.

EXAMPLES

Example 1

Initial Test on a Plasmid Target pcPNA Design and Binding Motif

The base pairs that are the basis of the pcPNA strategy, D:T and A:sU, are shown in FIG. 1a, along with the canonical A:T base pair. There is potential steric interference between the thio and amino groups of sU and D, respectively, in the apposition of sU and D, that prevents pairing between these analogs. Since sU and D can bind without steric hindrance to A and T, respectively, pcPNA pairs can bind cognate DNA but not each other. This property underlies the ability of pcPNAs to form double duplex strand invasion complexes on duplex DNA, as shown in FIG. 1.

Materials and Methods pcPNAs and Oligonucleotides

Boc-protected PNA monomers of 2-thiouracil and 2,6-diaminopurine were synthesized according to Lohse, et al., Proc. Natl. Acad. Sci. USA, 96:11804-11808 (1999). These monomers were used together with commercially available Boc-protected G and C PNA monomers (Applied Biosystems, CA). PNA oligomers were synthesized on a MBHA resin by standard procedures, purified by RP-HPLC, and characterized by MALDI-TOF mass spectrometry. DNA oligonucleotides were synthesized by Midland Certified Reagent Company (TX), using cyanoethyl phosphoramidite chemistry, and purified by HPLC.

For allele-specific PCR, the donor DNA is a 50-mer, single-stranded end-protected oligonucleotide that is homologous to the human beta-globin gene but introduces a 6-nucleotide mutation at the exon 2/intron 2 boundary.

Binding Assays

To assay for the double duplex invasion complexes, various concentrations of pcPNA1 and pcPNA2, as indicated, were incubated with a desired amount (0.5 µg) of pLSG3T7 in TE buffer (pH 7.4) with 10 mM KCl for 16 hr at 37° C. The pcPNAs-pLSG3T7 mixtures were then digested with two restriction enzymes (XhoI and BamHI), and analyzed by gel electrophoresis in 8% native polyacrylamide gels (19:1 acrylamide to bisacrylamide) using TBE buffer (90 mM Tris pH 8.0, 90 mM Boric acid, and 2 mM EDTA). DNA bands were visualized by silver staining.

Results

The ability of a pair of 10-mer pcPNAs (pcPNAs1 and pcPNA2; Table 1) to strand invade into and bind a plasmid target (pSupFLSG3T7) in vitro was investigated. Both of the pcPNAs were modified at the C and N-terminus by the addition of lysine residues to provide positive charges to enhance solubility. The two pcPNAs were incubated with the plasmid substrate and binding was assessed by cutting the target region from the plasmid by restriction enzyme digestion. The binding of the pcPNAs to the resulting linear fragment was visualized by gel mobility shift assay; binding. Binding of the pcPNA pair to the target is detected as the band of altered mobility that appears with increasing concentrations of pcPNAs.

Figure 3:
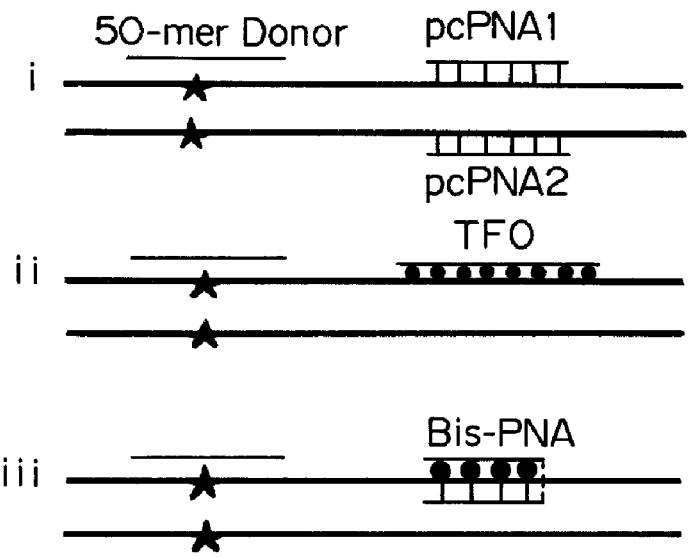
FIG. 3 is a diagram of recombination between a target gene and a single stranded donor DNA induced by selected DNA binding molecules: (i) pcPNAs, (ii) triplex-forming oligonucleotides (TFOs), and (iii) triplex-forming bis-PNAs.

TFOs and bis-PNAs have been shown to create altered helical structures that have been shown to induce recombination in mammalian cells (Rogers, et al., Proc. Natl. Acad. Sci. USA, 99:16695-16700 (2002)). As a model for gene correction, TFOs and bis-PNAs are able to stimulate recombination between a target gene and a DNA donor fragment in mammalian cells (FIGS. 3ii and 3iii).

Figure 4:
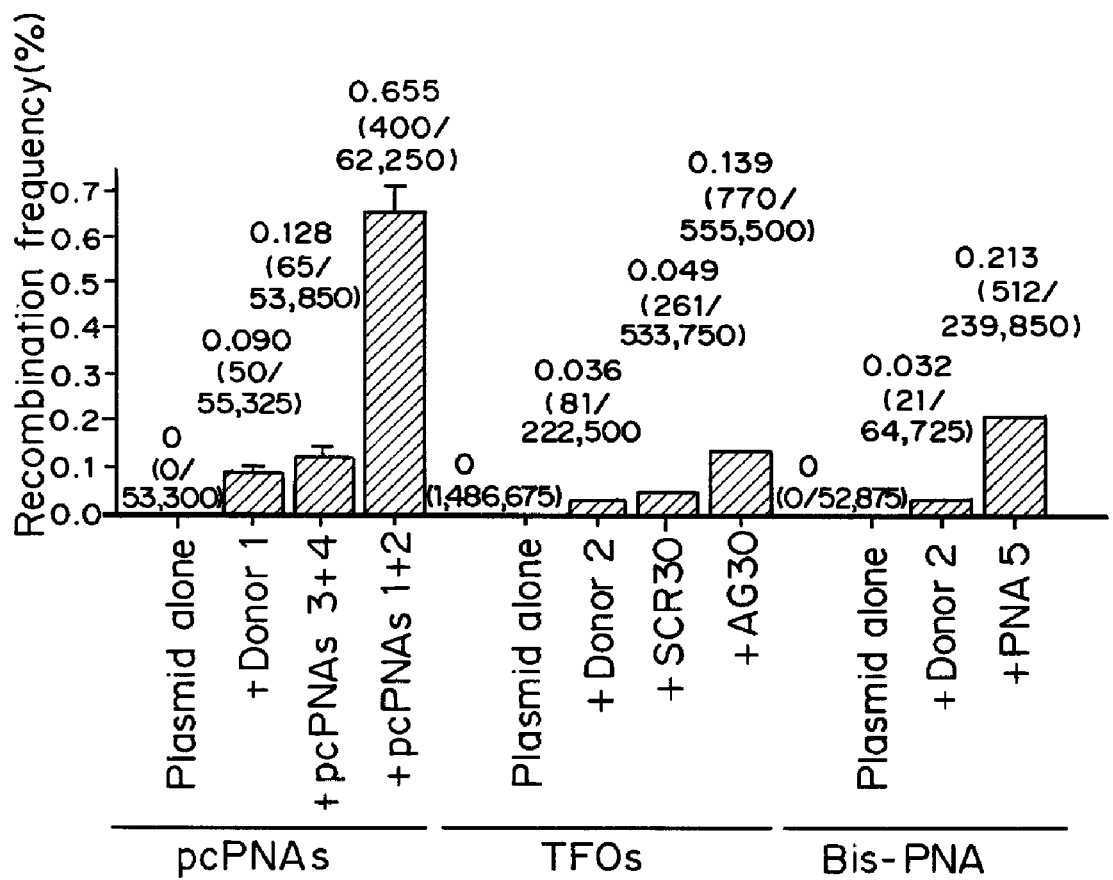
FIG. 4 is bar graph showing the frequency of correction of a point mutation in the supF reporter gene in the shuttle vector, psupFLSG3T7, (recombination frequency (%)) as function of selected DNA binding molecules in indicator bacteria. Molecules designed to bind to the supF gene include pcPNA1 and pcPNA2, which bind 62 by away from the mutation, the TFO (AG30), and the bis-PNA5 (PNA 5), which both bind 24 by away from the mutation to be corrected. Controls include plasmid alone, plasmid and donor without DNA binding molecules, mismatched pePNA3 and pcPNA4 (CTR-pcPNAs), and a mismatched DNA oligonucleotide (SCR30). The data represents at least three replicates in all cases, with standard errors as given.

To determine if the double duplex strand invasion complex formed by pcPNAs (FIGS. 1 and 3i) might constitute a helical alteration sufficient to provoke DNA repair and recombination, pcPNA1 and pcPNA2 were compared with TFOs and bis-PNA5 in an assay for induced recombination in mammalian cells (Table 1 and FIG. 4). In Table 1, PNAs are listed from N to C terminus. D: 2,6-diaminopurine, $^{S}$U: 6-thiouracil, O-8-amino-2,6-dioxaoctanoic acid. DNA sequences are written from 5' to 3'.

TABLE 1

| | Sequence of PNA and DNA oligomers |
|---|---|
| pcPNA1 | H-Lys-DCGDC$_S$UCDC$_S$U-Lys-NH$_2$ (SEQ ID NO: 1) |
| pcPNA2 | H-Lys-DG$_S$UGDG$_S$UCG$_S$U-Lys-NH$_2$ (SEQ ID NO: 2) |
| pcPNA3 | H-Lys-G$_S$UDGD$_S$UCDC$_S$U-Lys-NH$_2$ (SEQ ID NO: 3) |
| pcPNA4 | H-Lys-DG$_S$UGD$_S$UC$_S$UDC-Lys-NH$_2$ (SEQ ID NO: 4) |
| Bis-PNA5 | JJJJJTTJJT-O-O-O-TCCTTCCCCC-(Lys)$_3$ (SEQ ID NO: 5) |
| pcPNA6 | H-Lys-$_S$UD$_S$UGDCD$_S$UGDDC$_S$U-(Lys)$_4$-NH$_2$ (SEQ ID NO: 6) |
| pcPNA7 | H-Lys-DG$_S$U$_S$UCDC$_S$UG$_S$UCD$_S$UD-(Lys)$_4$-NH$_2$ (SEQ ID NO: 7) |
| PNA8 | H-Lys-TATGACATGAACT-(Lys)$_4$-NH$_2$ (SEQ ID NO: 8) |

TABLE 1-continued

Sequence of PNA and DNA oligomers

| | |
|---|---|
| PNA9 | H-Lys-AGTTCATGTCATA-(Lys)$_4$-NH$_2$ (SEQ ID NO: 9) |
| AG30 | AGGAAGGGGGGGTGGTGGGGAGGGGAG (SEQ ID NO: 10) |
| SCR30 | GGAGGAGTGGAGGGGAGTGAGGGGGGGGG (SEQ ID NO: 11) |
| supF1 Donor | TTCGAACCTTCGAAGTCGATGACGGGAGATTTAGA GTCTGCTCCCTTTGGC (SEQ ID NO: 12) |
| supF2 Donor | AGGGAGCAGACTCTAAATCTGCCGTCATCGACTTC GAAGG (SEQ ID NO: 13) |
| β-globin/GFP Donor | GTTCAGCGTGTCCGGCGAGGGCGAGGTGAGTCTAT GGGACCCTTGATGTTT (SEQ ID NO: 14) |
| β-globin donor | AAACATCAAGGGTCCCATAGGTCTATTCTGAAGTT CTCAGGATCCACGTG (SEQ ID NO: 15) |

In this assay, each targeting oligomer was designed, including the pair of pcPNAs, the TFO (AG30) and the bis-PNA (bis-PNA5), to bind to a selected site in the supF reporter gene contained in an SV40-based shuttle vector. In this vector construct, the supF gene has an inactivating single base pair mutation which can be corrected by recombination with a short single stranded oligonucleotide donor. The pcPNAs were designed to bind to a mixed sequence site 62 by away from the mutation, whereas the TFO and the bis-PNA were targeted to a G:C by rich polypurine site 24 by away from the mutation. The plasmid vector DNA was co-mixed with selected molecules, and the samples were transfected into monkey COS cells. Two days were allowed for repair/recombination/replication, and the episomal vector DNA was harvested for genetic analysis of the supF gene in indicator bacteria, as previously described (by Chan, et al., *J. Biol. Chem.*, 274:11541-11548 (1999)). As expected, and consistent with other published work, the TFO (AG30) and the bis-PNAS induced gene correction in the supF gene at frequencies of 0.14% and 0.21%, respectively (FIG. 4). The pcPNAs appeared to be were even more effective, inducing gene correction by the supF1-donor DNA at a frequency of 0.65%, more than seven-fold above the activity of the donor DNA alone (FIG. 4). This elevated frequency of induced recombination produced by the pcPNAs indicates that these molecules form highly recombinogenic structures when bound to duplex DNA. A pair of control pcPNAs (pcPNA3 and pcPNA4) with 5 mismatches each to the supF target site were ineffective, showing the sequence specificity of the process.

Example 2

Targeted Correction of a Thalassemia Associated Mutation in a Chromosomal Locus

Materials and Methods
Cells

The β-globin intron IVS2-1 (G→A) carrying a thalassemia-associated mutation or its wild-type equivalent IVS2 wt was inserted into the eGFP cDNA sequence of the pEGFP-N1 plasmid (Clontech, Palo Alto Calif.), between nucleotides 105 and 106, by PCR-based homologous recombination, resulting in pGFP/IVS2-1 and pGFP/IVS2 wt, respectively. The HinDIII-NotI fragments of these plasmids, containing the GFP sequence interrupted by IVS2-1 or IVS2 wt construct, were subcloned into the multiple cloning site of pcDNA5/FRT (Invitrogen, Carlsbad, Calif.), and the resulting vectors were stably transfected into CHO-Flp host cell lines using the Flp-In System according to manufacturer's instructions (Invitrogen, Carlsbad Calif.). Clones that had undergone single-copy integration at the expected site were isolated by selection and confirmed via Southern blot (data not shown). The resulting CHO-GFP/IVS2-1$^{G \rightarrow A}$ cells and control CHO-GFP/IVS2-1$^{WT}$ cells were grown in Ham's F12 media supplemented with 10% FBS and 2 mM L-glutamine.

Binding Assays

For the GFP-pcPNA binding assay, plasmid pBluescript 2-48 containing the target site for the pcPNA6 and pcPNA7 was generated by annealing the oligonucleotides 5'GAT-CATGGTTAAGTTCATGTCATA-3' (SEQ ID NO: 16) and 5'-AATTTATGACATGAACTTAACCAT-3' (SEQ ID NO: 17) and cloning them into the BamHI/EcoRI sites of pBluescriptII-SK (Stratagene, La Jolla, Calif.). The resulting plasmid DNA (1 μg) containing the binding site was incubated overnight with increasing concentrations of pcPNAs at 37° C. in TE buffer (pH 7.4) with 10 mM KCl. After incubation to allow plasmid:pcPNA complex formation, the samples were digested with PvuII to release a 400 by fragment, and binding was assayed by gel mobility shift as described above.

Transfection

1×10$^6$ cells in 100 μl of media were mixed with selected pcPNAs (6 μM) and GFP-DNA (12 μM) oligonucleotides and electroporated in 0.4 cm cuvettes using a Bio-Rad Gene Pulser (280V, 960 pFd, Hercules, Calif.). Cells were replated in 60 mm dishes following electroporation and allowed to expand to approximately 90% confluency (2-3 days). Chloroquine (100 μM) or Suberoylanilide hydroxamic acid (SAHA, 5 μM) were added after electroporation and media was replaced after 4 h. Two days later as indicated, cells were then visualized via fluorescence microscopy or analyzed by FACS.

Fluorescence Microscopy, FACS, and Live Flow Cytometry

Cells were visualized using a Zeiss Axiovert 200 (Thornwood, N.Y.) fluorescent microscope at 100× and 200× magnification. Cells for GFP FACS analysis were detached by trypsinization, washed once in 1×PBS, and fixed for at least 2 h at 4° C. in 2% paraformaldehyde in 1×PBS. Prior to FACS, the cells were pelleted and resuspended in PBS. Cells were analyzed using a Becton Dickinson FACS-Calibur flow cytometer (Franklin Lakes, N.J.). Live cell sorting of samples was performed at the Yale University Cell Sorter Facility using a Becton Dickinson FACSVantage SE flow cytometer, and cells were collected in Ham's F12 media supplemented with 20% FBS. Collected data were then analyzed using the FlowJo software (Tree Star Inc., Ashland, Oreg.).

RNA Isolation and Analysis

Total RNA was isolated from expanded GFP-positive flow-sorted cells using TRIzol Reagent (Invitrogen, Carlsbad, Calif.). Messenger RNA transcripts were then analyzed by reverse transcription-PCR (RT-PCR) on 50 ng purified total RNA with primers pJK115 (5'-AGCAAGGGCGAG-GAGCTGTTCACC-3') (SEQ ID NO: 18) and pJK118 (5'-CACTGCACGCCGTAGGTCAGGGT-3') (SEQ ID NO: 19) using the SuperScript One-Step RT-PCR kit (Invitrogen). The products were visualized by electrophoresis on a 1.7% TAE agarose gel. For CD34+ cell beta globin RT-PCR, primers were designed to anneal to exon sequences that flank IVS2.

Sequence Analysis of Genomic DNA

Genomic DNA was purified from expanded GFP-positive flow-sorted cells using the Wizard Genomic DNA Purification kit (Promega, Madison, Wis.), and the GFP-IVS2 region was amplified using primers pJK115 and pJK118, as above. The resulting PCR products were gel purified and sequenced with forward primer pJK115.

Results

The ability of pcPNAs to induce gene correction at a chromosomal site was also tested. An assay was developed in which the entire second intron of the human β-globin gene, carrying a thalassemia mutation at position 1 (IVS2-1, G:C to A:T), was inserted within the open reading frame of the green fluorescent protein (GFP) gene to fond a fusion gene designated GFP/IVS2-$1^{G \to A}$ (FIG. 2a). This GFP/IVS2-$1^{G \to A}$ construct was stably transfected into CHO cells to create a reporter cell line containing a single copy of the GFP/IVS2-$1^{G \to A}$ gene. The insertion was directed into a single, predefined locus by use of the CHO-Flp system (Knauert, et al., Mol. Therapy, 14:392-400 (2006)), and the new reporter cell line was designated as CHO-GFP/IVS2-$1^{G \to A}$. Single copy integration was confirmed by Southern blot (data not shown). The IVS2-1 mutation disrupts the normal β-globin splice site, and therefore expression of GFP requires correction of the IVS2-1 mutation so the β-globin intron can be spliced out of the GFP mRNA.

Figure 5:
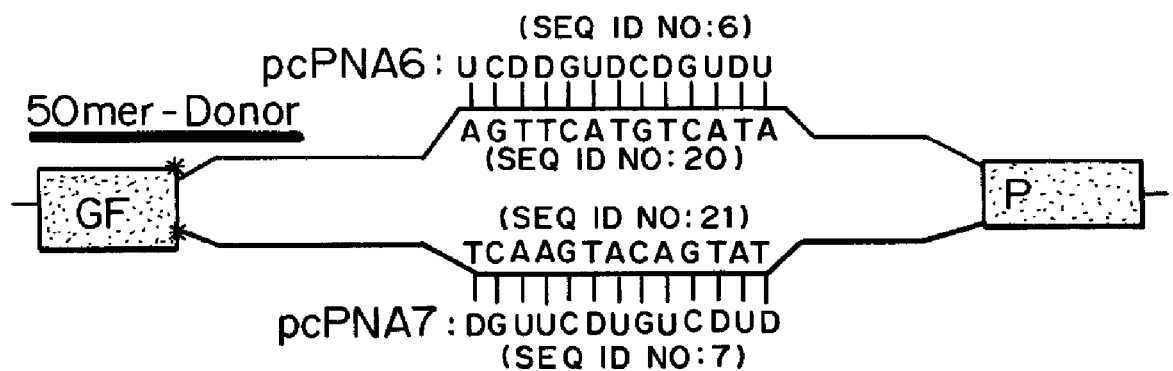
FIG. 5 is a schematic illustrating the experimental strategy to study pcPNA-induced recombination. The target region of a fusion gene containing the entire second intron of the human β-globin gene carrying a thalassemia-associated mutation at position 1 (IVS2-1, G:C to A:T) which disrupts the normal β-globin splice site, is depicted following formation of a double duplex induced by a pair of 13-mer pcPNAs, designated pcPNA6 and pcPNA7, designed to bind within the β-globin intron (at positions 51 to 64, a distance of 50 by from the splice site mutation) and to provoke recombination and gene correction by a co-transfected 51-mer single stranded donor DNA.

A pair of 13-mer pcPNAs, designated as pcPNA6 and pcPNA7 (FIG. 5 and Table 1) were designed to bind within the β-globin intron at positions 51 to 64, a distance of 50 by from the splice site mutation. Binding of the pcPNAs to the target site in the β-globin intron was confirmed in a gel mobility shift assay similar to that described above. A β-globin/GFP donor DNA was designed to correct the IVS2-1 G:C to A:T mutation to the wild-type sequence (FIG. 5). This 51-mer contained 25 nt of GFP sequence and 26 nt of β-globin sequence.

To test the ability of the pcPNAs to induce gene correction within β-globin sequences at a chromosomal site, the CHO-GFP/IVS2-$1^{G \to A}$ cells were transfected with β-globin/GFP donor DNA alone, β-globin/GFP donor DNA plus the β-globin pcPNAs (6 and 7), or β-globin/GFP donor DNA plus a pair of regular (non pseudo-complementary) PNAs of the same sequence (PNA8 and PNA9). Correction of the IVS2-1 G:C to A:T mutation was detected by the generation of green fluorescent cells which were quantified by FACS or fluorescent microscopy.

Figure 6:
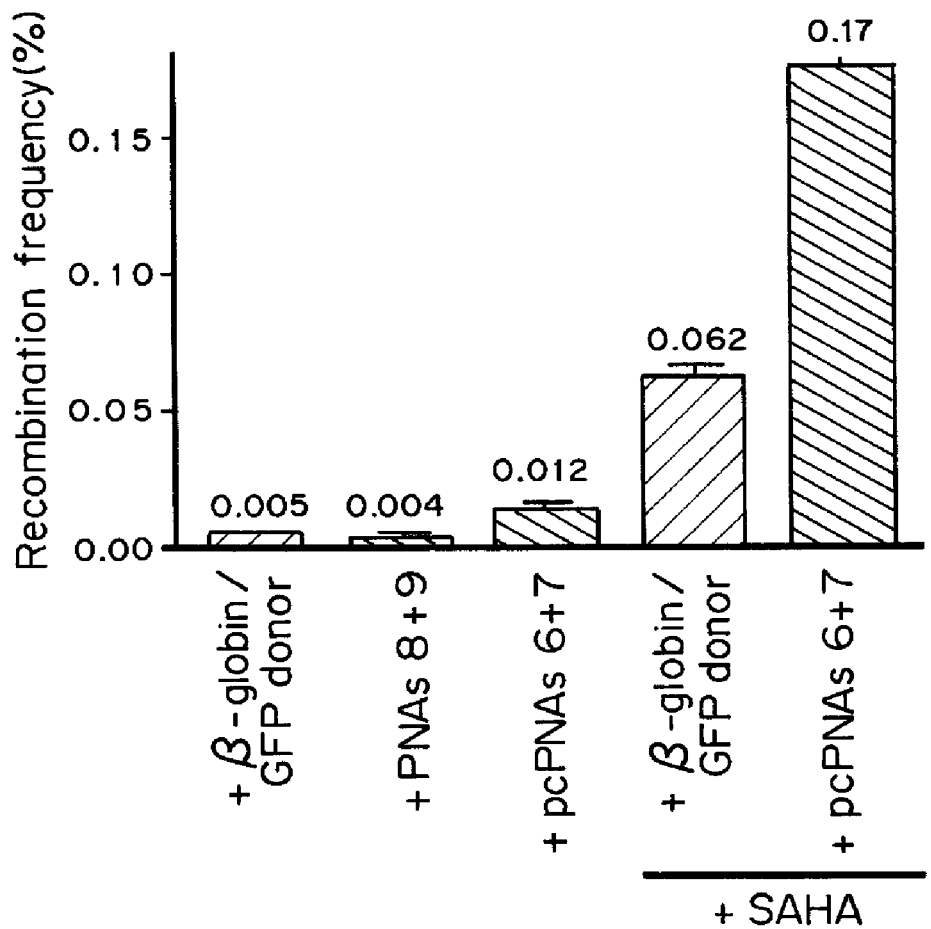
FIG. 6 is a bar graph illustrating induced recombination (Recombination Frequency (%)) in the chromosomal GFP/IVS2-1$^{G \rightarrow A}$ gene by electroporation-mediated transfection with selected molecules: β-globin/GFP donor alone, β-globin/GFP donor plus PNAs (non-pseudo-complementary PNA8 and PNA9 of the same sequence as pcPNA6 and pcPNA7), β-globin/GFP donor plus specific pcPNAs (pcPNA6 and pcPNA7), β-globin/GFP donor alone with the histone deacetylase inhibitor SAHA, or β-globin/GFP donor plus specific pcPNAs (pcPNA6 and pcPNA7) with the histone deacetylase inhibitor SAHA.

It was found that the combination of pcPNAs (6 and 7) with the β-globin/GFP donor DNA yielded a frequency of gene correction of 0.012% in a single transfection, 3-fold above the frequency seen with the β-globin/GFP donor DNA alone (FIG. 6). The differences in frequencies between the episomal and chromosomal targets, beyond the differences in the nature of the substrates, including accessibility, chromatin structure, and copy number can not be fully explained. In addition to the biological differences between episomal and chromosomal loci, two different sets of pcPNAs were used for these targets. The reason for this was to optimize the (A+T) content; binding sites with ≧40% A:T by are preferred. To meet this requirement, two different pairs of pcPNAs were designed and synthesized with slightly different lengths for the episomal and chromosomal targets.

Because previous studies with TFOs have suggested that the accessibility of chromosomal loci to binding molecules can vary with cell cycle phase (Wu, et al., Proc. Natl. Acad. Sci. USA, 102:2508-2513 (2005)) and transcriptional activity (Igoucheva, et al., Nucleic Acids Res., 31:2659-2670 (2003)), the possibility that modulation of chromatin/DNA interactions by treatment of cells with the histone deacetylase (HDAC) inhibitor, SAHA (an agent currently in clinical trials for cancer therapy), might increase the ability of the pcPNAs to target the GFP/IVS2-$1^{G \to A}$ fusion gene was tested. As shown, exposure of cells to SAHA substantially enhanced the gene correction frequencies, with the pcPNAs inducing gene correction at a frequency of 0.17%, a frequency again 3-fold above that seen with the donor alone under such conditions (FIG. 6).

Many factors affect gene correction frequency, such as the nature of the DNA binding molecules, their delivery to the nucleus, the accessibility and structure of the target region, and possibly the cell cycle. Also, different cell lines and different targets may provide for different targeting frequencies. Hence, the frequencies seen in the studies here are not directly comparable to the frequencies reported in other work using single-stranded oligonucleotides alone (Olsen, et al., J. Gene Med., 7:1534-1544 (2005)). The point is that whatever the baseline is of recombination mediated by single-stranded donor DNAs themselves, the use of pcPNAs can stimulate the level of recombination.

The pair of unmodified PNAs (PNA8 and 9), which have the same cognate sequence as β-globin-pcPNA6 and β-globin-pcPNA7, respectively, but are complementary to each other, had no effect above that of the GFP-donor DNA alone (0.004% vs. 0.005%). The inability of this pair to induce gene correction was expected since they should quench each other by forming a very stable PNA/PNA duplex. This finding indicates that a pair of unmodified PNAs cannot mediate sufficient strand invasion and target DNA binding to promote gene correction, a conclusion consistent with the model that a pair of pcPNAs is necessary to afford sufficient free energy to favor double-duplex invasion complex formation by binding the two target DNA strands simultaneously (Lohse, et al., Proc. Natl. Acad. Sci. USA, 96:11804-11808 (1999)). This demonstrates the importance of the pseudo-complementarity and provides direct evidence for pcPNA-induced recombination.

To validate the FACS analysis data, fluorescent microscopy of pcPNA6 and pcPNA7 and β-globin/GFP donor DNA-treated cells 48 hours after transfection, showed GFP-expressing CHO-GFP/IVS2-$1^{G \to A}$ cells in a field of predominantly GFP-negative, uncorrected cells. In selected samples, FACS was also used to obtain an enriched population of green cells produced by treatment of the CHO-GFP/IVS2-$1^{G \to A}$ cells with the pcPNAs and β-globin/GFP donor DNA. The RT-PCR analysis of the sorted cells was carried out in comparison to CHO cells containing the GFP gene with the wild-type beta-globin intron, and with the CHO cells containing the GFP gene with the mutated intron. RT-PCR of the correctly spliced mRNA results in a 209 by product, whereas the IVS2-1 splicing mutation yields a longer mRNA and produces a 256 by RT-PCR product. Gel electrophoresis of the RT-PCR product reveled that the CHO-GFP/IVS2-$1^{G \to A}$ cells with the mutant splice site have a larger RT-PCR product consistent with incorrect splicing, that is, use of an aberrant splice site almost 50 nt from the IVS2-1 site. The CHO-GFP/IVS2 wild type cells with the wild-type intron yield a smaller RT-PCR product, indicative of correct splicing out of the entire intron. The sorted cell populations show the correct (smaller) RT-PCR product, in keeping with the restoration of the wild-type splice site sequence at the IVS2-1 position, and consistent with the observed, acquired GFP expression by microscopy and FACS.

Figure 7:
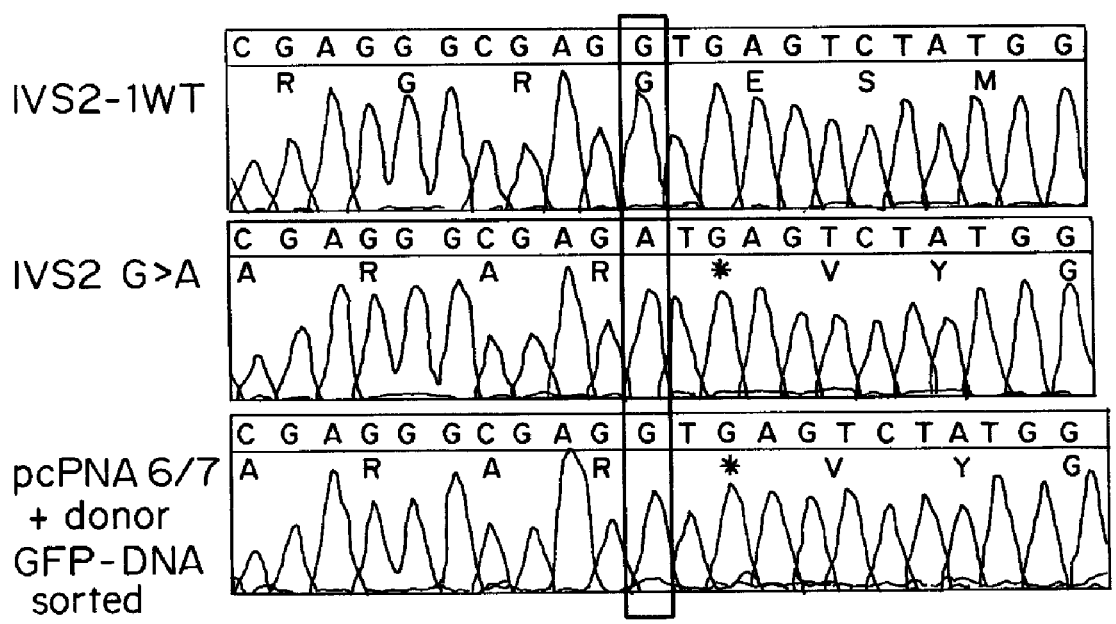
FIG. 7 is sequencing chromatograms depicting the genomic sequence at the target site of DNA collected from GFP-expressing sorted cells. Chromograms are from untreated CHO-GFP/IVS2$^{wt}$ cells containing the wild-type intron (top), untreated CHO-GFP/IVS2-1$^{G \rightarrow A}$ cells with the IVS2-1 G→A mutation (middle) and CHO-GFP/IVS2-1$^{G \rightarrow A}$ cells treated with pcPNAs and donor DNAs and sorted by FACS for GFP-expressing cells (bottom).

Finally, as another level of confirmation, genomic DNA was extracted and sequenced from sorted, GFP-positive cells that had been in culture for one month, to demonstrate the presence and persistence of the expected single base pair change at the genomic level (FIG. 7).

Example 3

Increased pcPNA-Mediated Gene Correction in Cells Synchronized in S-Phase

Materials and Methods
Cell Synchronization

Double thymidine addition was used for S phase synchronization. Thymidine was added to $1\times10^6$ cells in Ham's F12 media to a final concentration of 2 mM. Following a 12 h incubation period the thymidine-containing medium was replaced with normal culture medium, and the cells were grown for an additional 12 h to allow exit from S phase. The cells were grown again in medium containing 2 mM thymidine for another 12 h to synchronize the cells at the $G_1$/S border. The arrest was subsequently released by growing the cells in thymidine-free medium for 4-5 h to allow progression into S phase. Cell cycle profiles were determined by FACS, as above.

Results

Since manipulation of chromatin by the use of the HDAC inhibitor, SAHA, yielded an increased frequency of pcPNA-stimulated gene correction, selectively targeting cells in S-phase was also tested for improved gene correction (Majumdar, et al., *J. Biol. Chem.*, 278:11072-11077 (2003)).

The CHO-GFP/IVS2-$1^{G \rightarrow A}$ cells were synchronized in S-phase by double thymidine block (Zielke, et al., *Methods Cell Biol.*, 8:107-121 (1974)), yielding a cell population with 68% of the cells in S-phase. These cells were transfected with the β-globin-pcPNAs (6+7) plus β-globin/GFP donor DNA (or β-globin/GFP donor DNA alone) using electroporation. To attempt further optimization, replicate samples were also treated either with the lysosomotropic agent, chloroquine (which has been reported to enhance delivery of PNAs into cells) (Abes, et al., *J. Controll. Rel.*, 110:595-604 (2006)), or with the HDAC inhibitor, SAHA, has been found to promote increased levels of gene targeting in asynchronous cells (FIG. 6).

Figure 8:
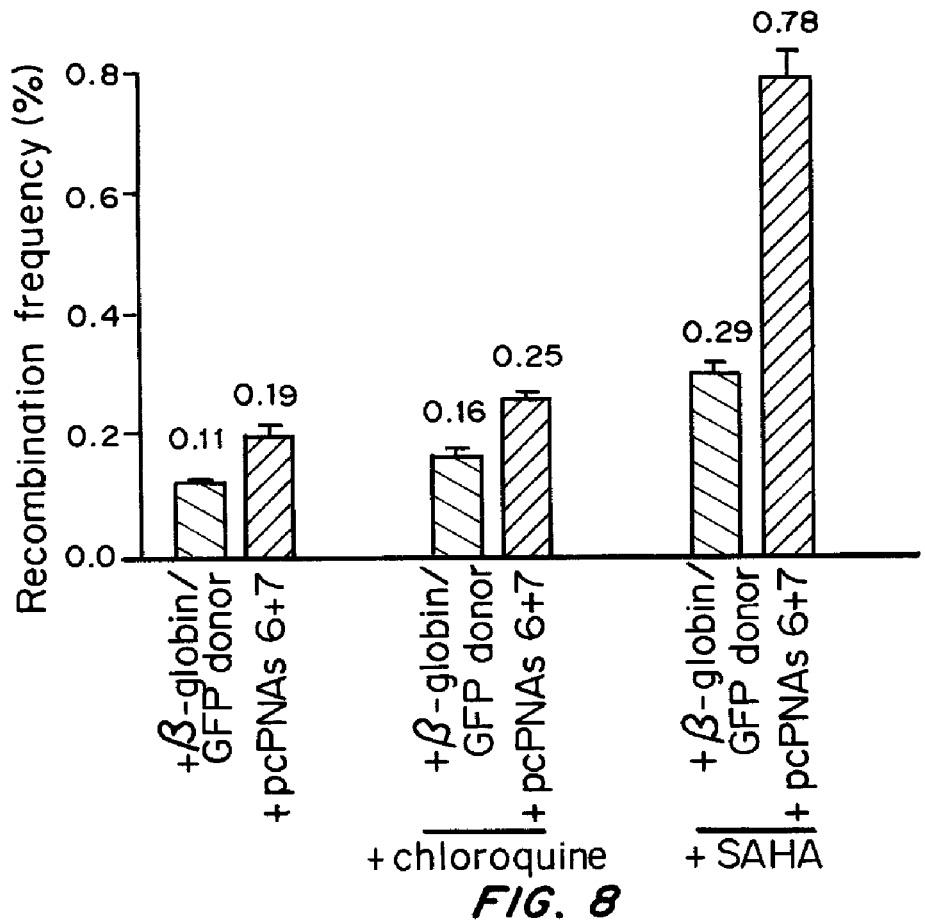
FIG. 8 is a bar graph showing induced recombination (Recombination Frequency (%)) in CHO-GFP/IVS2-1$^{G \rightarrow A}$ cells, synchronized in S-phase, that were transfected with β-globin/GFP donor DNA alone (hatched bars), or with the pcPNA6 and pcPNA7 plus β-globin/GFP donor DNA (solid bars) with, or without the addition of the endosomolytic agent, chloroquine, or with the histone deacetylase inhibitor, SAHA (as indicated). The bar graph represents data collected from at least 3 independent experiments, and with standard error indicated.

As shown in FIG. 8, S-phase synchronized cells are more susceptible to gene correction, with a frequency of 0.19% achieved with the combination of pcPNAs and β-globin/GFP donor DNA. When chloroquine was added, the induced gene correction frequency produced by pcPNAs was further elevated to 0.25%. However, a greater improvement was seen by the combination of cell synchronization and HDAC inhibition by SAHA, yielding a correction frequency of 0.78% in a single treatment, versus 0.29% with donor alone under the same conditions.

Example 4

Requirement for the Nucleotide Excision Repair Factor, XPA, in pcPNA-Induced Recombination Materials and Methods
Cells To study the role of nucleotide excision repair in pcPNA-stimulated recombination, two human fibroblast cell lines, the XPA-deficient XP12RO (homozygous for a nonsense mutation at Arg207) and its XPA-expressing subline, XP12RO/CL12 (kind gift from Richard Wood, University of Pittsburgh Medical School) were used. Cells were maintained in RPMI supplemented with 10% heat-inactivated fetal calf serum, 2 mM glutamine and 1% antibiotics (Invitrogen, Carlsbad, Calif.).

Transfection

For XP12RO and XP12RO/CL12, $1\times10^6$ cells were transfected with 4 uM beta globin donor DNA (Table 1) and 0 or 8 uM pcPNAs using the Amaxa Nucleofector according to manufacturer's instructions (Human fibroblast NHDF nucleofection kit, Amaxa Biosystems, Gaithersburg Md.), then placed in RPMI media containing 10% fetal bovine serum supplemented with G418 at a final concentration of 650 ug/mL (Invitrogen, Carlsbad Calif.). Cells were harvested 48 hours post-nucleofection by trypsinization, and then genomic DNA was extracted using the Wizard Genomic DNA Purification kit (Promega, Madison Wis.).

Allele-Specific PCR

Gene modification in XP12RO and XP12RO/CL12 cells treated with pcPNAs and beta globin donor DNA was assayed using allele-specific PCR, in which the 3' end of the forward primer corresponds to the wild-type or mutated sequence as introduced by the donor DNA. Equal amounts of genomic DNA were subjected to 40 cycles of 95° for 30 seconds, 62° (mutant allele-specific primer) or 64° (wild-type primer) for 30 seconds, and 72° for 1 minute, and the PCR products were electrophoresed on 1% agarose gels.

Results

The results above establish that pcPNAs can stimulate recombination and gene modification. It has been shown earlier that the ability of triplex formation to stimulate recombination depends on the nucleotide excision repair pathway and on the damage recognition factor, XPA. To study whether the NER pathway participates in pcPNA-induced gene modification, the recombination assay was preformed in two human fibroblast cell lines, the XPA-deficient cell line XP12RO (homozygous for a nonsense mutation at Arg207) and its XPA-expressing, complemented sublime, XP12RO/CL12. Cells were transfected with 4 uM donor DNA (designed to introduce a six by sequence change in the beta globin gene at the exon 1/intron 2 border) and 0 or 8 uM β-globin-pcPNA6 and pcPNA7, harvested 48 hours post-nucleofection by trypsinization, and then genomic DNA was extracted. Gene modification was assayed using allele-specific PCR, in which the 3' end of the forward primer corresponds to the wild-type or mutated sequence as introduced by the beta globin donor DNA. The results reveal that pcPNA and donor DNA were effective in inducing recombination only in XPA expressing cells. In the XPA-deficient cell line, no recombination was detected above the background.

These findings suggest that the ability of pcPNAs to induce recombination depends on the NER factor, XPA, and they support the hypothesis that the NER pathway can recognize pcPNA double duplex invasion complexes as lesions, thereby provoking DNA metabolism to yield recombino genic intermediates.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A recombinagenic or mutagenic composition comprising
    a pair of pseudocomplementary oligonucleotides having sequences that form a double duplex nucleic acid molecule with a target sequence of a double-stranded nucleic acid molecule, and
    a donor oligonucleotide essentially complementary to a recombination target sequence of the double-stranded nucleic acid molecule
    wherein the pair of pseudocomplementary oligonucleotides increase recombination of the donor oligonucleotide with the recombination target sequence compared to the donor oligonucleotide alone.

2. The composition of claim 1 wherein the donor oligonucleotide is single stranded.

3. The composition of claim 2 wherein the donor oligonucleotide is between 8 and 75 nucleotide residues in length.

4. The composition of claim 2 wherein the donor oligonucleotide contains one or more insertions, deletions, or substitutions relative to the recombination target sequence.

5. The composition of claim 1 wherein each of the pseudocomplementary oligonucleotides comprise between about 8 and 50 nucleobases.

6. The composition of claim 1 wherein the pseudocomplementary oligonucleotides and the donor oligonucleotide bind the double-stranded nucleic acid molecule at a distance of between about 25 and 75 nucleobases from each other.

7. The composition of claim 1 wherein the recombination target sequence of the double-stranded nucleic acid molecule is selected from the group consisting of a genomic DNA, a coding DNA sequence of a gene, an intron, a promoter, or an enhancer.

8. The composition of claim 7 wherein the gene is selected from the group consisting of an oncogene, a defective gene, and a viral gene.

9. The composition of claim 8 wherein the defective gene is selected from the group consisting of a defective β-hemoglobin gene, a cystic fibrosis gene, and a hemophilia gene.

10. The composition of claim 1 wherein the pseudocomplementary oligonucleotides are pseudocomplemetary peptide nucleic acids (pcPNAs) and the donor oligonucleotide is DNA.

11. The composition of claim 10 wherein the pcPNAs are synthesized with 2,6-diaminopurine (D) and 2-thiouracil (sU) nucleobases instead of adenines (A) and thymine (T).

12. A method for targeted recombination or mutation of a nucleic acid molecule comprising administering to cells or an individual an effective amount of a pharmaceutically acceptable therapeutic composition comprising
    a pair of pseudocomplementary oligonucleotides having a sequence that forms a double duplex nucleic acid molecule with a target sequence of double-stranded nucleic acid molecule, and
    a donor oligonucleotide essentially complementary to a recombination target sequence of the double-stranded nucleic acid molecule
    wherein the pair of pseudocomplementary oligonucleotides increase recombination of the donor oligonucleotide with the recombination target sequence compared to the donor oligonucleotide alone.

13. The method of claim 12 wherein the donor oligonucleotide is a single strand of DNA between 8 and 75 nucleotide residues in length.

14. The method of claim 13 wherein the donor oligonucleotide contains one or more insertions, deletions, or substitutions relative to the recombination target sequence.

15. The method of claim 12 wherein the pseudocomplementary oligonucleotides and the donor oligonucleotide bind the double-stranded nucleic acid molecule at a distance of between about 25 and 75 nucleobases from each other.

16. The method of claim 12 wherein the recombination target sequence of the double-stranded nucleic acid molecule is selected from the group consisting of a genomic DNA, a coding DNA sequence of a gene, an intron, a promoter, or an enhancer.

17. The method of claim 16 wherein the gene is selected from the group consisting of an oncogene, a defective gene, and a viral gene.

18. The method of claim 17 wherein the gene is selected from the group consisting of a defective β-hemoglobin gene, a cystic fibrosis gene, and a hemophilia gene.

19. The method of claim 12 wherein the pseudocomplementary oligonucleotides are pseudocomplemetary peptide nucleic acids (pcPNAs) comprising between about 8 and 50 nucleobases.

20. The method of claim 19 wherein the pcPNAs are synthesized with 2,6-diaminopurine (D) and 2-thiouracil (sU) nucleobases instead of adenines (A) and thymine (T).

21. The method of claim 12 further comprising co-administration of a second therapeutic agent selected from the group consisting of a histone deacetylase (HDAC) inhibitors and lysosomotropic agents.

* * * * *

UNITED STATES PATENT AND TRADEMARK OFFICE
CERTIFICATE OF CORRECTION

PATENT NO. : 8,309,356 B2
APPLICATION NO. : 12/753016
DATED : November 13, 2012
INVENTOR(S) : Peter M. Glazer Page 1 of 1

It is certified that error appears in the above-identified patent and that said Letters Patent is hereby corrected as shown below:

In the Specification

Column 1, Lines 14-16, replace "The Federal Government has certain rights in this invention by virtue of Grant Nos. R01CA64186 and RO1HL082655 from the National Institute of Health to Peter M. Glazer." with "This invention was made with government support under HL082655 and CA064186 awarded by National Institutes of Health. The government has certain rights in the invention."

Signed and Sealed this
Twenty-third Day of June, 2020

Andrei Iancu
*Director of the United States Patent and Trademark Office*